United States Patent [19]

Stima

[11] 4,360,021
[45] Nov. 23, 1982

[54] ABSORBENT ARTICLE
[75] Inventor: Joseph F. Stima, Edison, N.J.
[73] Assignee: Colgate-Palmolive Company, New York, N.Y.
[21] Appl. No.: 260,967
[22] Filed: May 6, 1981
[51] Int. Cl.³ ............................................ A61F 13/16
[52] U.S. Cl. .................... 128/287; 128/156; 128/290 R; 428/68; 428/72; 428/73; 428/116; 428/117; 428/178; 428/198; 428/913
[58] Field of Search ..................... 428/68, 72, 73, 116, 428/117, 118, 178, 296, 304, 402, 913, 198, 206, 211; 128/284, 290 R, 287, 156

[56] References Cited
U.S. PATENT DOCUMENTS 4,051,853 10/1977 Egan ................................. 128/287
4,055,180 10/1977 Karame ........................... 128/287
4,260,443 4/1981 Lindsay et al. ..................... 428/198

Primary Examiner—James J. Bell
Attorney, Agent, or Firm—Norman Blumenkopf; Murray M. Grill; Herbert S. Sylvester

[57] ABSTRACT

An absorbent article comprising a cover sheet and a backing sheet, the cover and backing sheets being attached in areas without the use of water-insoluble adhesives to form pockets in which a fluid absorbent material is stored. The absorbent article is formed by depositing portions of the fluid absorbent material on the backing sheet, placing the cover sheet over the absorbent material and the backing sheet, and pressing the cover sheet towards the exposed parts of the backing sheet to cause bonding of the fibers in each sheet and attaching the cover sheet to the backing sheet to form pockets in which the absorbent material is stored.

14 Claims, 11 Drawing Figures

ABSORBENT ARTICLE

BACKGROUND OF THE INVENTION

This invention relates to an absorbent article, and more particularly to an absorbent article having an improved construction. This invention also relates to a process of making such absorbent articles.

Numerous absorbent articles, such as disposable diapers and sanitary napkins, have been proposed for absorbing and retaining body fluids. Usually, the articles are constructed with an absorbent pad having a relatively large volume of pad material in order to provide the necessary absorbency and fluid holding capacity for the articles. As a result, such articles are undesirably bulky. For instance, disposable diapers are commonly made from a fluid impervious backing sheet, a fluid pervious cover sheet, and an absorbent pad, such as comminuted wood pulp known in the art as wood fluff, interposed between the backing and cover sheets. The pads of such conventional diapers are relatively bulky, particularly in the crotch region, resulting in a poor fit and minimal comfort to the wearer.

More recently, it has been proposed to use highly absorbent materials, such as hydrocolloid polymers, in the pads. In theory, the hydrocolloid materials permit a reduction in pad bulk while increasing desirable absorbent and fluid holding characteristic of the pads, since such materials are capable of absorbing and retaining many times their weight in liquids. However, in practice, the use of such materials in absorbent articles has been limited due to numerous difficulties brought forth by the materials themselves.

It is preferred that the hydrocolloid material be utilized in a particulate form, such as granules or flakes, in order to provide a greater exposed surface area for increased absorbency. However, it has been found that when placed in the pad, the particles migrate in the pads before the article has been used. Such particle migration may take place during packaging, storage, transportation, or other handling of the articles, resulting in movement of the particles from their initial location to remote parts of the pad where they are less effective.

In addition, when wetted, the hydrocolloid materials swell and become gelatinous. As a result, the materials migrate further in the pad when wetted, and cause the pad to become unstable. Thus, it has been found that the wetted materials cause the pad to shift, ball, split and shred during use of the articles.

Still more recently, an absorbent article comprising an absorbent pad assembly having an absorbent pad and pockets for retaining a hydrocolloid material in association with the pad is taught in U.S. Pat. No. 4,055,180 to Karami. According to this patent, two fluid impervious retaining sheets are attached to areas to define pockets in which the absorbent material is stored. Openings are provided in one of the retaining sheets to permit passage of the fluids into the pockets. Since the openings must be formed in the retaining sheet and adhesives are used to bond the retaining sheets together, such an absorbent article is not economically advantageous.

SUMMARY OF THE INVENTION

The present invention provides an absorbent article comprising a cover sheet and a backing sheet, the sheets being bonded in areas so as to define pockets in which an absorbent material is stored. The backing and cover sheets are bonded by pressing the fibers in the sheets together without the use of water-insoluble adhesives.

The present invention also provides a process of forming an absorbent article which comprises depositing a plurality of portions of an absorbent material on a backing sheet, the portions being separated from one another to expose the backing sheet; placing a cover sheet over the backing sheet and absorbent material; and pressing the cover sheet against the exposed parts of the backing sheet to bond the fibers in the sheets together, thus forming pockets in which the absorbent material is stored without the use of water-insoluble adhesives.

DETAILED DESCRIPTION OF THE INVENTION

According to the present invention, an absorbent article is provided in which the migration of granular, powder or flaked absorbents in diapers or sanitary napkins is prevented without the use of water-insoluble bonding agents. Furthermore, the present absorbent article provides room for the swelling of the absorbent material. As a result, the absorbent article of the present invention is less bulky, more comfortable to wear and less expensive to produce. It is preferred that no bonding agent at all be used to bond the sheets but solely a small amount of moisture to dampen the sheets which then when pressed together, presumable bond by hydrogen bonding forces.

To produce the present absorbent article, a liquid pervious backing sheet is placed on a flat horizontal surface. Portions of an absorbent material are deposited on the backing sheet, the portions being spaced or separated from one another in order to expose portions of the backing sheet. A cover sheet is then placed over the backing sheet and the absorbent material. Pressure is applied to the cover sheet against the exposed parts of the backing sheet to cause bonding of the fibers in the cover sheet and the backing sheet, thus forming sealed pockets in which the absorbent material is stored without the use of water-insoluble adhesives. It is not necessary in the present invention to use scrim guides to contain the absorbent material in pockets to hinder migration throughout the articles.

In depositing the absorbent material on the backing sheet, any convenient method may be used. However, the following procedure has been found to be particularly convenient and, therefore, is preferred.

Figure 1:
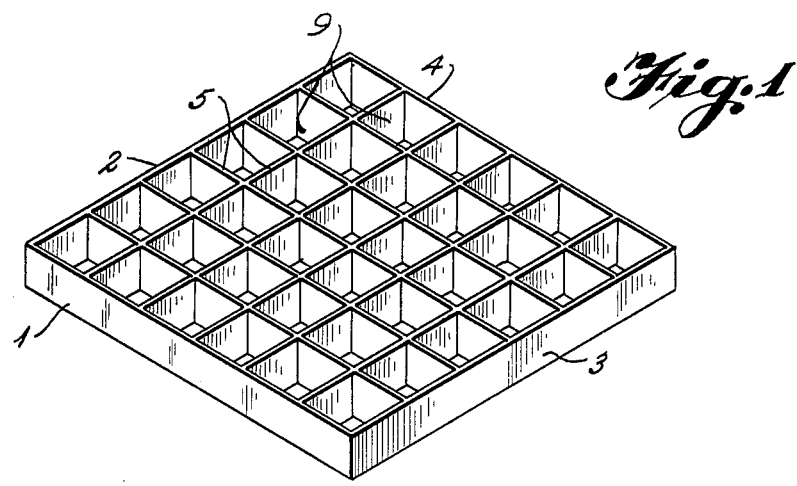
FIG. 1 illustrates a grid structure useful in the present invention.
Figures 2, 3:
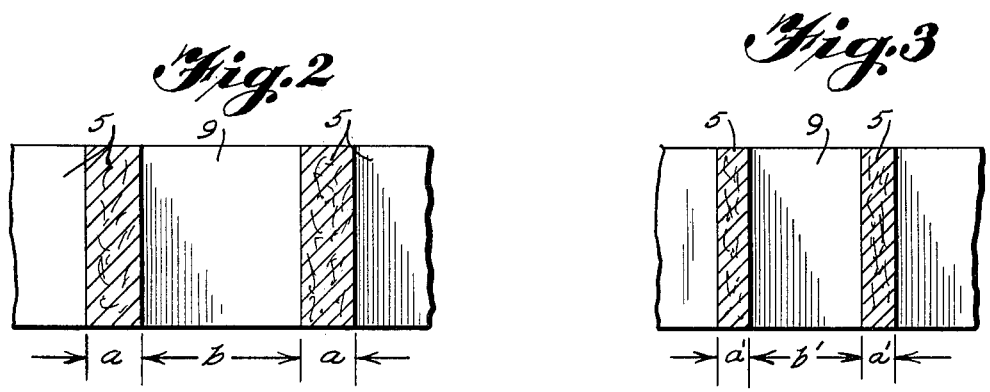
FIGS. 2 and 3 show cross-sectional views of openings in a grid structure.

According to this procedure, a grid-type structure is used to deposit the absorbent material on the backing sheet. FIG. 1 shows a typical grid structure which comprises a box-like structure having four side walls, 1, 2, 3 and 4. A plurality of dividing walls 5 are provided to define a plurality of openings 9 within the structure. It should be noted that the box-like structure and square openings shown in FIG. 1 are for illustration purposes only, it being understood that these can be replaced by any convenient design. The grid structure is placed on the backing sheet, with the longitudinal axis of the openings 9 in the grid structure being perpendicular to the backing sheet. As shown in FIG. 2, the ratio of the wall thickness "a" between the openings 9 to the width of the openings "b" (a:b) maybe from about 1:2 to about 1:50, preferably from about 1:10 to about 1:20. A suitable amount of an absorbent material is placed in each of openings 9 in the grid structure, after which the grid structure is removed. Thus, numerous portions of the absorbent materials are placed on the cover sheet in a spaced relationship. Thereafter, the cover sheet is placed over the absorbent material and the backing sheet. Preferably, the cover sheet is dampened by spraying with water. The amount of water introduced onto the cover sheet is not critical. However, the more water sprayed into the cover sheet, the longer it will take to dry the formed product. Thus, excess water should be avoided. The method by which water is introduced onto the cover sheet is not critical. Accordingly, the water may be sprayed directly onto the cover sheet. Thereafter, the same or different grid structure having a similar grid design but a smaller wall thickness between the openings, as in FIG. 3, is placed over the cover sheet, with the dividing walls 5 in the grid being aligned with the exposed portions of the backing sheet. The latter grid structure is preferred since the smaller wall thickness provides more space in the pockets so formed, thus allowing the absorbent material more room to expand upon being wetted. The ratio of the larger wall thickness ("a" in FIG. 2) to that of the smaller wall thickness ("a'" in FIG. 3) may range from about 10:1 to about 1.5:1, preferably from about 5:1 to about 2:1. The ratio of the wall thickness between the openings in the grid structure of FIG. 3 to the width of the openings at the widest point (a':b') may be from about 1:3 to about 1:100, preferably from about 1:12 to about 1:50. A suitable flat plate is placed over the grid to ensure even distribution of pressure. Pressure, ranging from about 5 p.s.i. to about 100 p.s.i., preferably from about 10 p.s.i. to about 50 p.s.i., is applied to the plate forcing it downwardly towards the backing sheet, thus causing the fibers in the sheets to bond and form a seal between the tissue sheets in the area beneath the dividing walls in the grid structure. If the cover sheet is dampened with water, a pressure of from about 5 p.s.i. to about 50 p.s.i., preferably from about 10 p.s.i. to about 25 p.s.i. can be used. Thereafter, the tissue laminate is removed and dried, if necessary.

In an alternative method, a foam pad is placed between the backing sheet and the flat surface at the beginning of the procedure. The absorbent material is deposited on the backing sheet as outlined in the preceeding paragraph. After the cover sheet has been placed on the absorbent material portions, a damp foam pad is placed over the cover sheet. If preferred, additional water is sprayed onto the top foam pad. As is readily apparent, any convenient method can be used to introduce water onto the cover sheet. Thereafter, pressure is applied to seal the cover and backing sheets.

Figure 4:
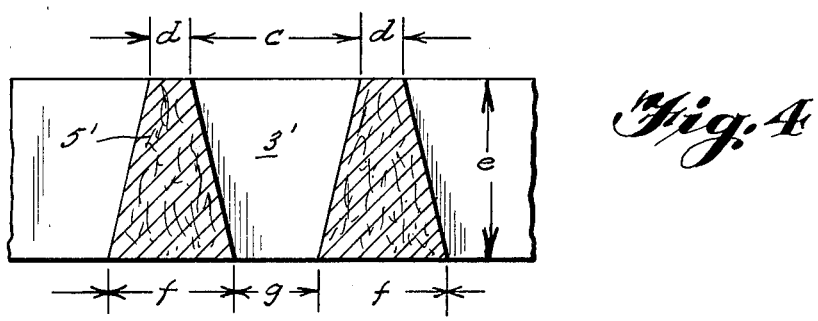
FIG. 4 shows the cross-sectional view of a grid structure having a tapered opening.
Figures 5, 6:
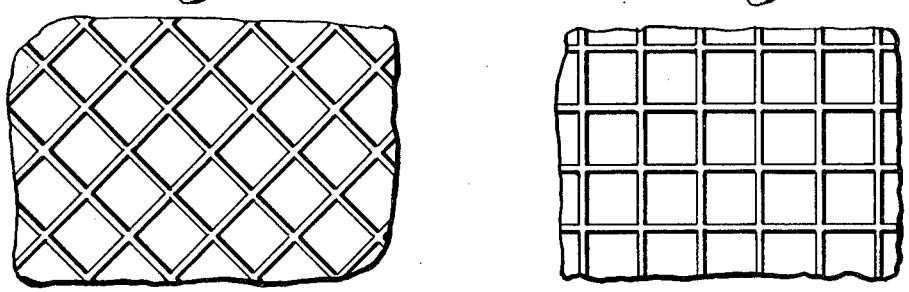
FIGS. 5-8 show various designs for a grid structure useful in the present invention.
Figure 7:
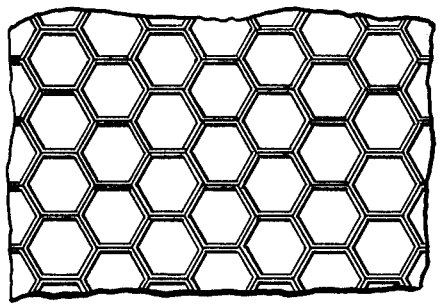
Figure 8:
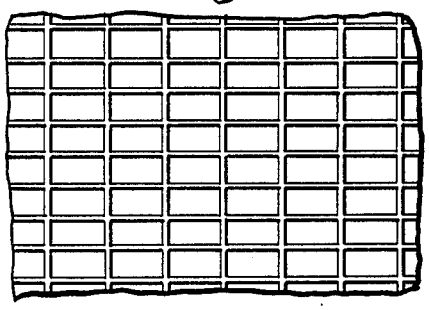

With reference to the grid structure used in forming the present absorbent article, it has been found that a grid structure wherein the openings are tapered is particularly useful. An example of such a grid structure is shown in FIG. 4. FIG. 4 shows that the wall thickness "f" between the openings in the grid structure on one side of the grid is larger than the other, "d". When depositing the absorbent material on the backing sheet, the side having the smaller opening "g" (or larger wall thickness between the openings) is placed on the backing sheet. After the deposition of the absorbent material, the other side of the grid, i.e., that having the larger opening "c" is placed on top of the cover sheet, after which pressure is applied to seal the sheets. By using a grid structure with such a tapered construction, the width of the areas "d" in which the two sheets are bonded is smaller than the width of the wall thickness "f", which means sufficient space is left in the pockets between the sheets to allow the absorbent material to swell without tearing the sheets apart. In this connection, the ratio (f:g) of the wall thickness between small openings "f" to the width of the small openings "g" maybe from about 1:1 to 1:5.

The ratio (c:d) of the width of the larger openings "c" to the wall thickness between larger openings "d" may be from about 3:1 to 100:1. The ratio and preferred ratios of the larger to smaller wall thicknesses (f:d) for the tapered grid are the same as those mentioned above for a:a' in FIG. 3.

With reference to the openings in the grid structure, it may have various designs, such as diamonds, squares, oblongs, and the like, as exemplified in FIGS. 5-8. In this connection, it will be appreciated that the function of the grid structure is to provide a plurality of compartments in which the absorbent material is placed. Thus, a wide variety of designs can be used, as long as the requirement that compartments are formed is satisfied. The grid structure may have any convenient dimensions in length, width and height and may be formed of any material which can withstand the pressure applied thereto.

As to the materials useful as the cover and backing sheets, cellulose tissue wadding may be mentioned. However, other liquid pervious hydrophilic materials capable of hydrogen bonding and well known in the art to be useful in the formation of absorbent materials can also be used. For instance, one or both of the sheets may be formed of cellulose fluff. In general the cover sheet is tissue wadding and the backing sheet is cellulose fluff or tissue wadding. The important factor regarding the cover and backing sheets is that the fibers are capable of strong bonds by virtue of hydrogen bonding when the sheets are pressed together. Other suitable materials include regenerated cellulose and other hydrophilic rayons.

As to the absorbent material for absorbing body fluid, hydrocolloid materials, i.e., materials which are capable of absorbing and retaining many times its weight in body fluid and which form a stable gel upon contacting the fluid, are preferred. Absorbent materials described in U.S. Pat. Nos. 3,070,095; 3,347,236; 3,645,836; 3,661,154; and 3,903,889 are exemplary of absorbent materials useful in the present invention. A particularly preferred material includes polysaccharide absorbent systems such as disclosed in pending commonly assigned patent applications: Ser. No. 104,204, filed: Dec. 17, 1979, now U.S. Pat. No. 4,333,461, entitled: "Borated Polysaccharide Absorbents and Absorbent Products" by E. G. Muller.

The disclosures of these patents and pending applications are incorporated herein by reference.

The absorbent material is preferably in the form of granules or flakes for greater available surface area. According to these pending applications, a preferred absorbent material comprises a mixture of a derivatized or underivatized cis-1,2-diol polysaccharide (e.g., guar gum), boric acid, and an alkali material or of a borate cross-linked guar gum and an alkali. When a derivatized material is used, the alkali may be separated from the absorbent material and deposited on the top surface of the backing sheet to provide delayed contact between the body fluid and the alkali material. Such delayed contact has been found to enhance the formation of a stable dilatant gel. The absorbent material may be used alone or it may be dispersed in a layer of fibrous absorbent material.

The amount of the absorbent deposited in each pocket may be varied. However, the amount of absorbent material should not fill the entire pocket since wetted absorbent material will swell.

The present absorbent article is useful in absorbing and retaining body fluids exuded by animals. Accordingly, the present absorbent article may be used as the absorbent core for such articles as diapers, sanitary napkins, bandages and surgical pads. In these instances, the present absorbent article is placed between a skin contacting layer which is liquid pervious and a liquid impervious layer, such as polyethylene. Alternatively, the present absorbent article may be formed into the final product by using the absorbent core, such as fluff, as the backing sheet. Generally, the present absorbent article is disposable, i.e., it is discarded after being used once. The present absorbent article may also be used in conventional disposable diaper and sanitary napkin structures utilizing said article as an additional absorbent means. In such structures the present absorbent article may be placed between the top sheet and conventional fluff pad; behind the fluff pad or even in the middle of a split fluff pad. In the latter case the article would in order of the layers from skin contacting surface to the outside might be (1) top sheet, (2) wadding sheet (may be omitted), (3) conventional layer of wood fluff, (4) absorbent grid of the present invention, (5) second conventional wood fluff layer, (6) wadding sheet (may be omitted) and (7) polyethylene backing sheet. Typical diaper constructions may be found in U.S. Pat. No. 4,051,853 to Egan, Jr. and U.S. Pat. No. 4,069,822 to Buell.

Figure 9:
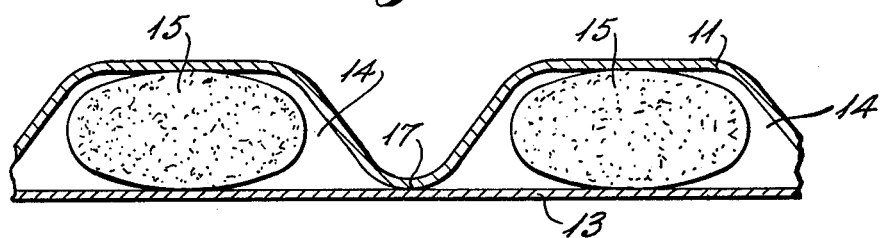
FIGS. 9-11 show the cross-sectional views of various constructions for the present absorbent article.
Figure 10:
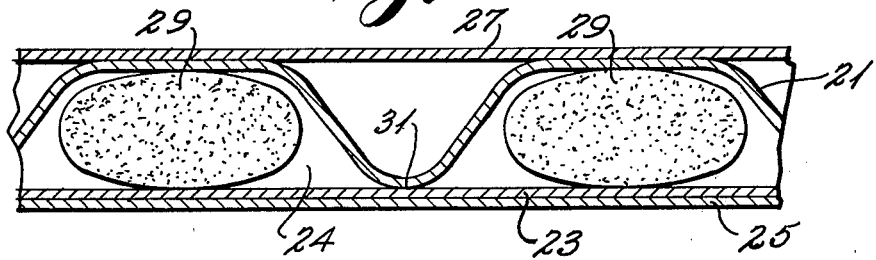
Figure 11:
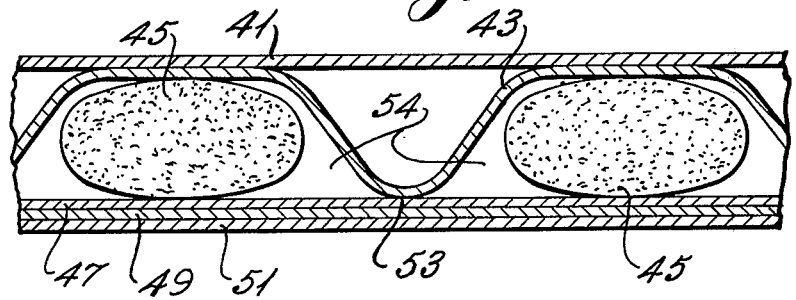

Cross-sectional views of typical constructions of the present absorbent articles are shown in FIGS. 9-11. In FIG. 9, a plurality of absorbent material portions 15 are interposed between cover sheet 11 and backing sheet 13 in the pocket 14. The alkali may be separated from the absorbent material and deposited on the top surface of backing sheet 13. Cover sheet 11 is bonded to backing sheet 13 at a plurality of locations represented by numeral 17. Cover sheet 11 and backing sheet 13 may be made of the same or different material. Useful materials include tissue wadding and cellulose fluff.

In FIG. 10, a plurality of portions of absorbent material 29 is placed between cover sheet 21 and back sheet 23 in pocket 24. The alkali in the absorbent material may instead be deposited on the top surface of backing sheet 23. Cover sheet 21 is bonded to backing sheet 2 at a plurality of locations 31. Top sheet 27 is a liquid pervious layer which contacts the wearer's skin. Accordingly, the top sheet is made of material which is non-toxic and will not irritate the wearer's skin. Outer layer 25 is made of a liquid impervious material such as nylon or polyethylene which prevents the penetration of body fluid from striking through the absorbent article. Sheets 21 and 23 may be formed of the same or different materials, examples of which include cellulose tissue wadding, cellulose fluff or regenerated cellulose.

FIG. 11 illustrates another embodiment of the present absorbent article. A plurality of absorbent material portions 45 are interposed between cover sheet 43 and backing sheet 47. The alkali in the absorbent material may be separately deposited on the top surface of backing sheet 47. Sheets 43 and 47 are bonded together at a plurality of locations as indicated at 53. Top sheet 41 is formed of non-toxic, non-irritating material well known in the art since this sheet comes in direct contact with the wearer's skin. Sheet 49 is formed of cellulose fluff and is disposed between backing sheet 47 and liquid impervious outer sheet 51. Liquid pervious sheets 43 and 47 may be formed of the same or different material such as tissue wadding and cellulose fluff. Outer sheet 51 may be formed of a liquid impervious material such as polyethylene, nylon, and the like.

It is noted that in the constructions shown in FIGS. 9-11, the body fluid which flows into the absorbent article through the top layer or layers is absorbed by the absorbent material. Liquid which enters the article at locations where no absorbent material is present (e.g., location 53 in FIG. 11) is rapidly channelled to the sides and undersides of pockets 54 which provides optimum contact of absorbent material and body fluid. In addition the body fluid is also rapidly channelled to the fluff 49. Thus highly efficient absorption of body fluid is obtained using the present absorbent article.

Also, there is provided an absorbent article in which the migration of granular, powder or flaked absorbent materials is prevented without the use of water-insoluble adhesives or scrim. As a result, an improved absorbent article having a lower manufacturing cost and improved structure is obtained.

The present invention is further illustrated in the following non-limiting examples.

EXAMPLE 1

A pad of ¼ inch polyurethane foam is placed on a work bench. A sheet of tissue wadding is overlayed on the foam pad. A grid structure having square openings is placed on top of the tissue sheet. The openings in the grid are tapered, with the side with the larger wall thickness between the openings being placed down (i.e., towards the tissue sheet). A pre-determined amount of the absorbent material is distributed through the grid onto the tissue. Thereafter the grid is removed. Another tissue is overlayed on the absorbent material and the backing sheet. A damp sheet of 1/32 inch foam is placed over the system. The grid is then overlayed in the same position as initially but in this instance, the side of the grid having the smaller wall thickness between the openings is placed down. A piece of plywood is placed over the grid. A pressure of 15 p.s.i. is applied to the plate to force it down toward the sheet, thus forming a seal between the tissue sheets in the grid area. The tissue sandwich is removed from the system and dried.

EXAMPLE 2

The procedure in Example 1 is repeated with the exception that the damp sheet of 1/32 inch foam is wetted further by spraying with water.

EXAMPLE 3

Example 1 is repeated with the exception that the backing sheet is replaced by a layer of wood fluff.

The absorbent material used in Examples 1 to 3 is that obtained in Example 1 of copending application Ser. No. 104,204 filed Dec. 17, 1979 by Muller.

EXAMPLE 4

A diaper is prepared utilizing a conventional top sheet and polyethylene backsheet but in place of a wood fluff pad there is used an absorbent grid as produced in Example 1. About 10 grams of absorbent is uniformly distributed in the grid pockets. The assembled diaper in flat-out condition (i.e., before box-pleating) is about 30 cm×48 cm and weighs about 15 grams. The produce performs excellently for absorbing a baby's urine.

EXAMPLE 5

Example 1 is repeated, except that the damp sheet of foam is, instead of being dampened with water alone, is dampened with a 0.05% water solution of gum acacia.

EXAMPLE 6

Example 5 is repeated using a 0.5% solution of polyvinyl alcohol (water-soluble 88% hydrolyzed polyvinyl acetate).

While the invention herein has, in the main, been described, and a preference stated for the use of water alone to effect bonding of the grid sheets through, as postulated, in a major way, the hydrogen bonding between the hydrophilic fibers of the cellulosic material, there has also been exemplified the use of the auxiliary use of minor amounts of water-soluble adhesives. Such adhesives are well known and include the dextrins, natural gums (arabic, acacia and the like), polyvinyl alcohol, water-soluble acrylates and other water-soluble homopolymeric and interpolymeric materials, pectins, guar gum and the like. Generally such auxiliary binders are used in very minor amounts e.g., as 0.01 to 2% and preferably 0.5 to 1% aqueous solutions.

What is claimed is:

1. An absorbent article comprising a liquid pervious backing sheet having deposited thereon a plurality of substantially uniformly distributed discrete portions of absorbent material, each of said absorber portions being substantially identical in cross section and separated from adjacent of said absorber portions by a base sheet portion having a width W, a cover sheet bonded to said base sheet uniformly along a width portion $W_1$ substantially symetrically disposed within said width W, the ratio of $W:W_1$ being from about 1.5:1 to 10:1, said base and cover sheets so bonded defining a plurality of pocket portions encasing each of said absorber portions within a volume exceeding that occupied by each of said absorber portions thereby enabling the latter to swell when wet.

2. A product according to claim 1 coherein the wherein of $W:W_1$ is 2:1 to 5:1.

3. A product according to claim 1 wherein said absorber portions are substantially cylindrical.

4. A product according to claim 1 wherein said absorbent material comprises a mixture of (a) a derivatized or underivatized cis-1,2-diol polysaccharide, boric acid and an alkali material or (b) a borate cross-linked guar gum and alkali.

5. A product according to claim 4 wherein said alkali is initially provided on the top surface of said backing sheet.

6. The absorbent article of claim 1 wherein the absorbent material comprises a mixture of borate cross-linked guar gum and an alkali.

7. The absorbent article of claim 6 wherein the absorbent material is dispersed in a layer of fibrous absorbent material.

8. The absorbent article of claim 1 wherein the absorbent material comprises a mixture of derivatized or underivatized guar gum, boric acid and an alkali.

9. The absorbent article of claim 8 wherein the absorbent material is dispersed in a layer of fibrous absorbent material.

10. An absorbent article comprising a liquid impervious backing layer, a skin contacting liquid pervious layer, and interposed between said layers the absorbent article of claim 1.

11. The article of claim 9 which is in the form of a diaper.

12. The article of claim 9 which is in the form of a surgical pad.

13. The article of claim 9 which is in the form of a bandage.

14. The article of claim 9 which is in the form of a sanitary napkin.

* * * * *